(12) United States Patent
Dowling et al.

(10) Patent No.: US 6,258,925 B1
(45) Date of Patent: Jul. 10, 2001

(54) POLYESTER POLYCONDENSATION WITH TITANYL OXALATE CATALYST AND A CATALYST ENHANCER

(75) Inventors: Conor M. Dowling, Blue Bell; Sri R. Seshadri, Holland, both of PA (US)

(73) Assignee: ATOFINA Chemicals, Inc., Philadelphia, PA (US)

( * ) Notice: Subject to any disclaimer, the term of this patent is extended or adjusted under 35 U.S.C. 154(b) by 0 days.

(21) Appl. No.: 09/747,115

(22) Filed: Dec. 22, 2000

Related U.S. Application Data

(60) Provisional application No. 60/175,006, filed on Jan. 7, 2000.

(51) Int. Cl.⁷ .............................. C08G 63/02; B01J 31/00
(52) U.S. Cl. ......................... 528/279; 528/275; 528/285; 528/308.1; 528/308.3; 502/103; 502/113; 502/118; 502/161; 502/170
(58) Field of Search ..................... 528/275, 279, 528/285, 308.1, 308.3; 502/103, 113, 118, 161, 170

(56) References Cited

U.S. PATENT DOCUMENTS

| | | |
|---|---|---|
| 3,907,754 | 9/1975 | Tershansy et al. . |
| 3,951,886 | 4/1976 | Miyake et al. . |
| 4,238,593 | 12/1980 | Duh . |
| 4,245,086 | 1/1981 | Ono et al. . |
| 4,356,299 | 10/1982 | Cholod et al. . |
| 5,198,530 | 3/1993 | Kyber et al. . |

FOREIGN PATENT DOCUMENTS

| | | |
|---|---|---|
| 0 699 700 A2 | 3/1996 | (EP) . |
| 42-13030 | 7/1967 | (JP) . |
| 6-128464 | 5/1994 | (JP) . |

OTHER PUBLICATIONS

R. E. Wilfong, "Linear Polyesters," Journal of Polymer Science, pp. 385–410, (1961).

F. Piliti, Comprehensive Polymer Science, Chapter 17 "Polyesters", pp. 275–315 (1989).

*Primary Examiner*—Samuel Acquah
(74) *Attorney, Agent, or Firm*—Nicholas J. DeBenedictis; Stanley A. Marcus

(57) ABSTRACT

The present invention is based upon the discovery that nontitanyl oxalates can enhance the catalytic functionality of titanyl oxalate catalysts. This invention provides a novel catalytic composition containing a titanyl oxalate catalyst and a metallic oxalate catalyst enhancer and optionally containing a metallic cocatalyst such as an antimony based catalyst. A synergistic relationship has been discovered between titanyl oxalate catalyst and the catalyst enhancer. A synergistic relationship has also been discovered between the titanyl oxalate catalyst, catalyst enhancer and a metallic cocatalyst such as antimony oxide or antimony triacetate. Also provided is an improved process of producing polyester by the polycondensation of polyester forming reactants in the presence of a catalytically effective amount of a polycondensation catalyst, wherein the improvement comprises utilizing, as the polycondensation catalyst, the novel catalyst composition containing a titanyl oxalate such as lithium titanyl oxalate and a catalyst enhancer such as a nontitanyl metallic oxalate like lithium oxalate and optionally containing a metallic catalyst such as antimony oxide or antimony triacetate. The improved process produces an improved polyester having lower acetaldehyde numbers and good color. The titanyl oxalate/catalyst enhancer composition can be used as a polycondensation catalyst in combination with other catalysts to achieve synergistic catalytic activity. Preferred is a combination of lithium titanyl oxalate, $Li_2TiO(C_2O_4)_2$, lithium oxalate, $Li_2(C_2O_4)_2$ with antimony oxide or antimony triacetate or antimony trisglycoxide.

23 Claims, No Drawings

POLYESTER POLYCONDENSATION WITH TITANYL OXALATE CATALYST AND A CATALYST ENHANCER

REFERENCE TO RELATED APPLICATION

The present application claims priority of U.S. Provisional Application No. 60/175,006, filed Jan. 7, 2000.

BACKGROUND OF THE INVENTION

This invention relates to a method for manufacturing polyesters, in particular, to using a titanyl oxalate, such as lithium titanyl oxalate, as the catalyst for such reaction in combination with a catalyst enhancer such as a metallic oxalate like lithium oxalate to provide fast reactions with improved properties such as reduced acetaldehyde content and good color properties for the resulting polyester at substantially reduced catalyst levels. A synergistic relationship has been discovered between titanyl oxalate catalyst and the catalyst enhancer. A synergistic relationship has also been discovered between the titanyl oxalate catalyst, catalyst enhancer and a metallic cocatalyst such as antimony oxide or antimony triacetate.

DESCRIPTION OF THE PRIOR ART

Polycondensation reactions that produce polyesters require an extremely long period of time that is significantly reduced by a suitable catalyst. Various types of catalysts are used to shorten the reaction time. For example, antimony trioxide antimony triacetate and antimony trisglycoxide are generally used as polycondensation catalysts.

Titanyl oxalate compounds have been suggested as catalysts for polycondensation reactions to produce polyesters. However, titanyl oxalate catalysts when used as polycondensation catalysts for polyesters have caused color problems in the resulting polyester.

Polyesters are obtained by esterification, ester interchange or polycondensation of dibasic acids such as terephthalic acid and isophthalic acid or esters thereof, functional derivatives of acid chlorides and glycols such as ethylene glycol and tetramethylene glycol or oxides thereof and functional derivatives of carbonic acid derivatives. In this case, a single polyester is obtained when one dibasic acid component and glycol component is used. Mixed copolyesters can be obtained when at least two or more types of dibasic acid component and glycol component are mixed, esterified or subjected to ester interchange and then subjected to polycondensation. When a single polyester or two or more initial polycondensates of a mixed copolyester are subjected to polycondensation, an ordered polyester is obtained. In this invention, the term polyester is a general designation for these three types.

Prior literature has disclosed titanyl oxalate compounds for use as polycondensation catalysts for polyesters. The titanyl oxalate compounds disclosed include potassium titanyl oxalate, ammonium titanyl oxalate, lithium titanyl oxalate, sodium titanyl oxalate, calcium titanyl oxalate, strontium titanyl oxalate, barium titanyl oxalate, zinc titanyl oxalate and lead titanyl titanate. However, based upon the examples in such literature references, only potassium and ammonium titanyl oxalate have actually been used to catalyze the polyester forming reaction. See for example Japanese Patent Publication 42-13030, published on Jul. 25, 1967. European Patent application EP 0699700 A2 published Mar. 6, 1996 assigned to Hoechst and entitled "Process for production of Thermostable, Color-neutral, Antimony-Free Polyester and Products Manufactured From It" discloses the use as polycondensation catalyst, however only potassium titanyl oxalate and titanium isopropylate were used for such a catalyst, and, while improved color and antimony free polyester are disclosed, cobalt or optical brighteners were also employed. Other patents have disclosed potassium titanyl oxalate as a polycondensation catalyst for making polyester such as U.S. Pat. No. 4,245,086, inventor Keiichi Uno et al., Japanese Patent JP 06128464, Inventor Ishida, M. et al. U.S. Pat. No. 3,957,886, entitled "Process of Producing Polyester Resin" of Hideo, M. et al, at column 3, line 59 to column 4, line 10, contains a disclosure of titanyl oxalate catalysts for polyesters including a listing of many types of titanyl oxalate catalyst. However, only potassium titanyl oxalate and ammonium titanyl oxalate were used in the examples and lithium titanyl oxalate was not even listed among their preferred titanyl oxalate catalysts.

SUMMARY OF THE INVENTION

The present invention is based upon the discovery that nontitanyl oxalates can enhance the catalytic functionality of titanyl oxalate catalysts. This invention provides a novel catalytic composition containing a titanyl oxalate catalyst and a metallic oxalate catalyst enhancer and optionally containing a metallic cocatalyst such as an antimony based catalyst. A synergistic relationship has been discovered between titanyl oxalate catalyst and the catalyst enhancer. A synergistic relationship has also been discovered between the titanyl oxalate catalyst, catalyst enhancer and a metallic cocatalyst such as antimony oxide or antimony triacetate. Also provided is an improved process of producing polyester by the polycondensation of polyester forming reactants in the presence of a catalytically effective amount of a polycondensation catalyst, wherein the improvement comprises utilizing, as the polycondensation catalyst, the novel catalyst composition containing a titanyl oxalate such as lithium titanyl oxalate and a catalyst enhancer such as a nontitanyl metallic oxalate like lithium oxalate and optionally containing a metallic catalyst such as antimony oxide or antimony triacetate. The improved process produces an improved polyester having lower acetaldehyde numbers and good color. The titanyl oxalate/catalyst enhancer composition can be used as a polycondensation catalyst in combination with other catalysts to achieve synergistic catalytic activity. Preferred is a combination of lithium titanyl oxalate, $Li_2TiO(C_2O_4)_2$, lithium oxalate, $Li_2(C_2O_4)_2$ with antimony oxide or antimony triacetate.

DETAILED DESCRIPTION OF THE INVENTION

The production of polyester by polycondensation of polyester forming reactants is well known to those skilled in the polyester art. A conventional catalyst for the reaction is antimony oxide. The present invention is based upon the discovery of a synergistic relationship between titanyl oxalate catalysts and metallic oxalate catalyst enhancer (e.g. lithium oxalate) is surprisingly superior in catalyst performance for polycondensation reactions by producing polyesters of superior color (white) in comparison to other titanyl oxalate catalysts. The need for an antimony containing catalyst can thereby be eliminated, and an antimony free polyester can thereby be produced with lithium titanyl oxalate as the catalyst. Such advantages provided by using lithium titanyl oxalate are retained when lithium titanyl oxalate is used in combination with other polycondensation catalysts for producing polyester as long as lithium titanyl oxalate comprises at least 1 parts per million (preferably 1 to 20) based on the weight of titanium in the reaction mixture. Included within the meaning of the term "lithium titanyl oxalate" as used herein are di lithium titanyl oxalate [$Li_2TiO(C_2O_4)_2$] and mono lithium titanyl oxalate wherein one of the lithiums of di lithium titanyl oxalate is replaced with another alkaline metal such as potassium (e.g., LiKTiO ($C_2O_4$)$_2$) and such compounds with or without water of hydration. Lithium titanyl oxalate catalysts can be combined with antimony catalyst to achieve the benefits of both catalysts when elimination of antimony is not a requirement for the resulting catalyzed product.

In addition to enhancing the catalytic effect of titanyl oxalates for catalyzing polycondensation reactions, the metallic oxalates can enhance the catalytic effectiveness of titanyl oxalates for catalyzing esterification and transesterification reactions when used in catalytically effective amounts with reactants known to participate in esterification or transesterification reactions. A catalytically effective amount is suitable. Preferred is about 3 parts of titanyl oxalate based on the weight of titanium per million parts of esterification or transesterification reaction mixture.

Reactants for forming polyesters via a polycondensation reaction are well known to those skilled in the art and disclosed in patents such as U.S. Pat. No. 5,198,530, inventor Kyber, M., et al., U.S. Pat. No. 4,238,593, inventor B. Duh, U.S. Pat. No. 4,356,299, inventor Cholod et al, and U.S. Pat. No. 3,907,754, inventor Tershasy et al, which disclosures are incorporated herein by reference. The art is also described in "Comprehensive Polymer Science, Ed. G. C. Eastmond, et al, Pergamon Press, Oxford 1989, vol. 5, pp.275–315, and by R. E. Wilfong, J. Polym. Science, 54(1961), pp.385–410. A particularly important commercial specie of polyester so produced is polyethylene terephthalate (PET).

Titanyl Oxalates: Titanyl oxalates include metallic titanyl oxalates [$M_2TiO(C_2O_4)_2(H_2O)_n$] wherein each M is independently selected from potassium, lithium, sodium and cesium such as lithium or potassium titanyl oxalate and nonmetallic titanyl oxalates such as ammonium titanyl oxalate. The titanyl oxalate may be anhydrous (n=0) or contain some water of hydration, i.e. n representing the amount of water of hydration.

Non Titanyl Oxalates: Nontitanyl oxalates that function as catalytic enhancers for titanyl oxalate catalysts include lithium oxalate, $Li_2C_2O_4$, sodium oxalate, $Na_2C_2O_4$, potassium oxalate, $K_2C_2O_4$, rubidium oxalate, $Rb_2C_2O_4$, cesium oxalate, $Cs_2C_2O_4$. Preferred is lithium oxalate.

Cocatalyst: Cocatalysts that function in combination with the titanyl oxalate catalyst and the metallic oxalate enhancer include antimony triacetate, $Sb(CH_3COO)_3$, antimony glycoxide, $Sb_2(OCH_2CH_2O)_3$, antimony oxide ($Sb_2O_3$).

An effective amount for enhancing the catalytic activity of titanyl oxalate catalysts is at least about 1 part of metallic oxalate per part of titanyl oxalate catalyst. Preferred is from about 1 part to about 100 parts enhancer per part of catalyst based upon the total weight of titanyl oxalate catalyst and cocatalyst if any.

A catalytically effective amount of titanyl oxalate is added to the polyester forming reactants. Preferred is from about 1 part to about 40 parts per million of catalyst based on the weight titanium in the catalyst and the weight of the of polyester forming reactants, which is about the same as 1 part of 40 parts per million by weight catalysts in the resulting polyester based upon the weight of titanium in the catalyst The synergistic performance of the catalyst enhancer in combination with one or more catalysts for a polycondensation reaction for the production of PET resin is shown by the following examples.

EXAMPLES

Catalyst evaluation was performed with a 3/16 stainless steel, 1.5 L reactor, fitted with an extrusion screw at the base of the reactor. The vessel was equipped with 3 inlet ports and was vertically stirred with an electric motor with amperage monitoring. The laboratory experimental were all conducted on a 4.0 mole scale, using as polyester forming reactants, BHET and a normal bottle resin autoclave recipe. The experimental catalysts were added at the time of BHET charging.

Bis(2-hydroxyethyl)terephthalate (BHET) and catalyst were added to the reactor and the contents blanketed with nitrogen. The mixture's were heated under reduced pressure with constant stirring. The EG produced during the polymerization was removed and trapped. The polymerization was stopped when the stirrer torque reached a level, indicated by amperage to the stirrer motor, typical for a polymer of IV ~0.6.

Seventeen examples were performed using the above procedure and various catalyst and catalyst enhancer amounts.

Example A catalyst–240 ppm antimony from antimony oxide ($Sb_2O_3$)–reaction time=127 mins Example B catalyst 10 ppm titanyl from lithium oxalate– reaction time=100 mins Example 1 catalyst–10 ppm titanyl from lithium oxalate+ 146 ppm lithium oxalate (or approximately 15 equivalents)– reaction time=53 mins Example 2 catalyst–10 ppm titanium from lithium titanyl oxalate+735 ppm lithium oxalate (or approximately 70 equivalents)–reaction time=55 mins Example C catalyst–6 ppm titanium from lithium titanyl oxalate+75 ppm antimony from antimony oxide ($Sb_2O_3$)— reaction time=105 mins Example D catalyst–6 ppm titanium from lithium titanyl oxalate+150 ppm antimony from antimony oxide–reaction time=110 mins Example 3 catalyst–6 ppm titanium from lithium titanyl oxalate+75 ppm antimony from antimony oxide+367 ppm lithium oxalate (or approximately 15 equivalents)–reaction time=65 mins Example 4 catalyst–3 ppm titanium from lithium titanyl oxalate+38 ppm antimony from antimony oxide+184 ppm lithium oxalate (or approximately 35 equivalents)–reaction time=90 mins Example 5 catalyst–2.6 ppm titanium from lithium titanyl oxalate+33 ppm antimony from antimony oxide+160 ppm lithium oxalate–reaction time=110 mins Example 6 catalyst–3 ppm titanium from lithium titanyl oxalate+38 ppm antimony from antimony oxide+185 ppm lithium oxalate–reaction time=95 mins Example 7 catalyst–3.3 ppm titanium from lithium titanyl oxalate+41 ppm antimony from antimony oxide+146 ppm lithium oxalate–reaction time=70 mins Example 8 catalyst–2.0 ppm titanium from lithium titanyl oxalate+25 ppm antimony from antimony oxide+90 ppm lithium oxalate–reaction time=120 mins Example 9 catalyst–4.7 ppm titanium from lithium titanyl oxalate+59 ppm antimony from antimony oxide+118 ppm lithium oxalate–reaction time=100 mins Example 10 catalyst–2.0 ppm titanium from lithium titanyl oxalate+25 ppm antimony from antimony oxide+50 ppm lithium oxalate–reaction time=125 mins Example 11 catalyst–2.0 ppm titanium from potassium titanyl oxalate+25 ppm antimony from antimony oxide+90 ppm potassium oxalate–reaction time=115 mins Example 12 catalyst–2.0 ppm titanium from potassium titanyl oxalate+25 ppm antimony from antimony oxide+50 ppm lithium oxalate–reaction time=165 mins Example E catalyst–240 ppm antimony from antimony oxide, commercial color adjustment included–reaction time=110 mins Example Results and Discussion Catalysts with enhancer were found to give improved productivity, higher brightness, higher yellowness, and in most cases, reduced acetaldehyde (AA) levels in the polymer.

In comparing example B with example 1, the addition of lithium oxalate to lithium titanyl oxalate provided a doubling of the polymerization rate achieved with lithium oxalate alone. The polymers formed had similar color, acetaldehyde concentration and CEG number. The addition of an extra quantity of lithium oxalate as in the case of example 2, relative to that present in example 1, did not further increase the polymerization rate. Indicating the presence of a synergistic relationship between lithium titanyl oxalate and lithium oxalate. In comparing examples B, 1, and 2 with example A, a higher polymerization rate was observed for the former at lower metal loading than example A, with similar polymer IV, CEG number, acetaldehyde concentration and higher L* and b* values for the former.

In comparing example C with example 3, the addition of lithium oxalate to a mixture of lithium titanyl oxalate and antimony oxide, substantially increased the polymerization rate. Providing polymers with similar CEG number and acetaldehyde concentration. However example 3 gave a polymer with higher L* and lower b* values than that produced by example C.

In comparing example C with example 4, where the levels of titanium and antimony have been halved, the addition of lithium oxalate in example 4 provides for a higher polymerization rate at 50% of the titanium/antimony loading, giving direct evidence for the ability of lithium oxalate to enhance the catalytic activity of the titanium and antimony catalyst mixture. Also, the concentration of acetaldehyde in the polymer produced with example 4 is considerably lower than that of example C. The color has also improved as indicated by the change in L* and b* values.

In comparing examples 5 through 12, which consist of mixtures of titanyl oxalates, metal oxalates and antimony oxide, with example E, which is antimony oxide with the addition of a commercial color adjustment. Similar polymerization rates are observed for all examples. However, the 3 component catalyst mixtures of examples 5 through 12 all have considerably reduced metal loading. Also, the acetaldehyde concentration in the polymers produced with examples 5–12 is lower (by up to 50%) then that observed for the control, example E, with the polymers produced having good color.

The addition of commercial color adjustment to the antimony oxide control, example E, has the effect of reducing both the L* and b* values (i.e. brightness and yellowness) of the polymer produced. If commercial color adjustment had not been added to this control the L* and b* values of the polymer produced would have similar values to those obtained for examples 5 through 12.

The most preferred catalyst is that catalyst mixture of example 10. It gave good color (L* and b*), equivalent polymerization time vs. control, and considerably reduced AA in PET at low catalyst levels.

Increasing polymerization throughputs, reduction of acetaldehyde in packaging resins, and cost effective reduction of antimony and of total catalyst are some of the advantages of the present invention as shown be the examples.

Results of the seventeen examples are given in the Table below. Noteworthy is that all of the catalysts (with the exception of example 12) demonstrated improved productivity in BHET polymerization in comparison to standard antimony catalyst of example A and E. All produced brighter but more yellow products, and that CEGs for all batches fell in the range 17±7, which is typical for our lab autoclave runs. Acetaldehyde values for titanium-containing polymers are typically higher than for antimony-containing polymers. However, it was noted that catalyst examples 4 through 12 produced polymer with significantly reduced acetaldehyde compared to the antimony controls which were achieved at very low catalyst levels (25% or less metal content when compared to the control).

The examples are in two sets. Examples A–D and 1–4 relate to the synergy between lithium titanyl oxalate and lithium oxalate, lithium titanyl oxalates and lithium oxalate and antimony which lead to a much improved polymerization rate. Examples E and 5–12 indicate that when the amounts of the 3 components are optimized, they produced a catalyst with equivalent rate to the control at considerably reduced metal loading, with polymer produced having good color and reduced AA content.

| CATALYST | AMOUNT | POLY TIME | IV | CEG | AA | L* | b* |
|---|---|---|---|---|---|---|---|
| A | .292 gms. | 127 mins. | 0.679 | 16 | 99 ppm | 68.1 | 7.8 |
| B | .063 gms. | 100 mins. | 0.674 | 16 | 95 ppm | 78.4 | 26.1 |
| 1 | .212 gms. | 53 mins. | 0.666 | 18 | 112 ppm | 75.9 | 28.3 |
| 2 | .810 gms. | 55 mins. | 0.683 | 18 | 136 ppm | 72.9 | 31.2 |
| C | .128 gms. | 105 mins. | 0.644 | 17 | 126 ppm | 75.9 | 28.1 |
| D | .220 gms. | 110 mins. | 0.694 | 18 | 128 ppm | 72.8 | 22.5 |
| 3 | .501 gms. | 65 mins. | 0.68 | 14 | 106 ppm | 79.8 | 21.1 |
| 4 | .250 gms. | 90 mins. | 0.628 | 24 | 47 ppm | 80.46 | 20.1 |
| 5 | .220 gms. | 110 mins. | 0.599 | 11 | 38 ppm | 53.7 | 39.4 |
| 6 | .253 gms. | 95 mins. | 0.590 | 13 | 37 ppm | 48.3 | 39.8 |
| 7 | .220 gms. | 70 mins. | 0.576 | 10 | 29 ppm | 54.7 | 39.8 |
| 8 | .135 gms. | 120 mins. | 0.603 | 13 | 43 ppm | 48.4 | 41.9 |
| 9 | .220 gms. | 100 mins. | 0.597 | 12 | 41 ppm | 51.5 | 43.6 |
| 10 | .094 gms. | 125 mins. | 0.602 | 13 | 26 ppm | 48.9 | 38.3 |
| 11 | .137 gms. | 115 mins | 0.598 | 13 | 28 ppm | 43.4 | 53.9 |
| 12 | .096 gms. | 165 mins. | 0.581 | 16 | 19 ppm | 45.4 | 49.3 |
| E | .292 gms. | 110 mins. | 0.599 | 14 | 48 ppm | 29.9 | −4.2 |

L* relates to brightness, the closer the value to 100 the brighter the polymer. Compare L* of 80.5 for 3 component catalyst (example 4) to that for antimony oxide at 68.1 (example A).
The b* measurement relates to degree of yellow coloration of polymer, the lower the b* value the less yellow the polymer. Compare 3 component catalyst (example 4) b* value of 20.1 to antimony oxide at 7.8 (example A)

Concentration of acetaldehyde: AA is an undesirable polymerization by-product. Compare 3 component catalyst (example 10) AA levels of 26 ppm to that observed for antimony oxide control (example E), 48 ppm.

Polymerization rate: rate at which the IV increases during reaction, measurement taken in this case when IV was approximately 0.6. Compare 3 component catalyst (example 4) producing polymer with IV>0.6, reaction time 90 minutes. Antimony oxide (example A) producing polymer with IV>0.6, with reaction time 127 minutes.

Intrinsic viscosity (IV): indication of the degree of polymerization that has occurred during the reaction. IV of 0.6 indicates a number average molecular weight of ~19,000.

CEG: carboxyl end group, indication of the number of acid end groups per unit weight polymer. Compare 3 component catalyst (example 10) producing polymer with CEG level of 13 with antimony oxide with CEG level of 14. Indicating that the polymers produced with both systems are very similar structurally.

Catalyst concentration: 3 component catalyst of example 10 produced polymer containing 34 ppm metal derived from catalyst, compared to polymer produced from antimony oxide containing 240 ppm metal derived from catalyst.

We claim:

1. An enhanced titanyl oxalate catalyst composition comprising titanyl oxalate and an effective amount of a nontitanyl metallic oxalate for enhancing the catalytic effectiveness of the titanyl oxalate.

2. An enhanced catalyst composition comprising a titanyl oxalate, a metallic catalyst and an effective amount of a nontitanyl metallic oxalate for enhancing the catalytic effectiveness of the titanyl oxalate.

3. The composition of claim 1 wherein the metallic oxalate is selected from the group consisting of lithium oxalate, $Li_2C_2O_4$, sodium oxalate, $Na_2C_2O_4$, potassium oxalate, $K_2C_2O_4$, rubidium oxalate, $Rb_2C_2O_4$, and cesium oxalate, $Cs_2C_2O_4$.

4. The composition of claim 1 wherein the titanyl oxalate is selected from the group consisting of metallic titanyl oxalates of the formula $M_2TiO(C_2O_4)_2(H_2O)_n$ wherein each M is independently selected from potassium, lithium, sodium, cesium and a nonmetallic cation such as ammonium.

5. The composition of claim 1 wherein the metallic oxalate is lithium oxalate and the titanyl oxalate is lithium titanyl oxalate.

6. The composition of claim 2 wherein the metallic catalyst is selected from the group consisting of antimony triacetate, $Sb(CH_3COO)_3$, antimony trisglycoxide, $Sb_2(OCH_2CH_2O)_3$, antimony oxide ($Sb_2O_3$).

7. The composition of claim 1, wherein the metallic oxalate comprises from 1 part to 80 parts by weight of the composition.

8. The composition of claim 2, wherein the metallic oxalate comprises from 1 part to 80 parts by weight of the composition.

9. The composition of claim 3, wherein the metallic oxalate comprises from 1 part to 80 parts by weight of the composition.

10. The composition of claim 4, wherein the metallic oxalate comprises from 1 part to 80 parts by weight of the composition.

11. The composition of claim 5, wherein the metallic oxalate comprises from 1 part to 80 parts by weight of the composition.

12. The composition of claim 6, wherein the metallic oxalate comprises from 1 part to 80 parts by weight of the composition.

13. An improved process of producing a polyester by the catalyzed polycondensation of polyester forming reactants in the presence of a polycondensation catalyst, wherein the improvement comprises utilizing as the catalyst the composition of claim 1.

14. An improved process of producing a polyester by the catalyzed polycondensation of polyester forming reactants in the presence of a polycondensation catalyst, wherein the improvement comprises utilizing as the catalyst the composition of claim 2.

15. An improved process of producing a polyester by the catalyzed polycondensation of polyester forming reactants in the presence of a polycondensation catalyst, wherein the improvement comprises utilizing as the catalyst the composition of claim 3.

16. An improved process of producing a polyester by the catalyzed polycondensation of polyester forming reactants in the presence of a polycondensation catalyst, wherein the improvement comprises utilizing as the catalyst the composition of claim 4.

17. An improved process of producing a polyester by the catalyzed polycondensation of polyester forming reactants in the presence of a polycondensation catalyst, wherein the improvement comprises utilizing as the catalyst the composition of claim 5.

18. An improved process of producing a polyester by the catalyzed polycondensation of polyester forming reactants in the presence of a polycondensation catalyst, wherein the improvement comprises utilizing as the catalyst the composition of claim 6.

19. An improved polyester containing the composition of claim 1.

20. The improved polyester of claim 19 wherein the composition of claim 1 comprises from 1 part to 40 parts per million of the polyester.

21. The improvied polyester of claim 20 wherein the polyester is polyethylene terephthalate.

22. An improved polyester containing the composition of claim 2.

23. The improved polyester of claim 22 wherein the polyester is polyethylene terephthalate and the composition of claim 2 is as defined in claim 6.

* * * * *